(12) United States Patent
Hillen et al.

(10) Patent No.: US 10,327,614 B2
(45) Date of Patent: Jun. 25, 2019

(54) DEVICE FOR TREATING A SURFACE

(71) Applicant: Vorwerk & Co. Interholding GmbH, Wuppertal (DE)

(72) Inventors: Lorenz Hillen, Wuppertal (DE); Mara Brandt, Bielefeld (DE)

(73) Assignee: Vorwerk & Co. Interholding GmbH, Wuppertal (DE)

( * ) Notice: Subject to any disclaimer, the term of this patent is extended or adjusted under 35 U.S.C. 154(b) by 0 days.

(21) Appl. No.: 15/743,389

(22) PCT Filed: Jul. 4, 2016

(86) PCT No.: PCT/EP2016/065693
§ 371 (c)(1),
(2) Date: Jan. 10, 2018

(87) PCT Pub. No.: WO2017/016813
PCT Pub. Date: Feb. 2, 2017

(65) Prior Publication Data
US 2018/0199781 A1 Jul. 19, 2018

(30) Foreign Application Priority Data
Jul. 27, 2015 (DE) .................. 10 2015 112 174

(51) Int. Cl.
*A47L 9/28* (2006.01)
*A47L 11/40* (2006.01)
(Continued)

(52) U.S. Cl.
CPC ......... *A47L 9/2826* (2013.01); *A47L 11/4011* (2013.01); *G01N 21/4738* (2013.01);
(Continued)

(58) Field of Classification Search
CPC ........ A47L 9/28; A47L 9/2826; A47L 9/2831; A47L 11/40; A47L 11/4011;
(Continued)

(56) References Cited

U.S. PATENT DOCUMENTS

| 8,719,998 | B1 | 5/2014 | Huffman | |
| 2014/0166047 | A1* | 6/2014 | Hillen | ............ A47L 9/30 134/6 |

FOREIGN PATENT DOCUMENTS

| DE | 10 2013 113 426 A1 | 6/2014 |
| EP | 2 515 196 A2 | 10/2012 |
| WO | 2007/028049 A2 | 3/2007 |

OTHER PUBLICATIONS

International Search Report of PCT/EP2016/065693, dated Oct. 11, 2016.

\* cited by examiner

*Primary Examiner* — Jamil Ahmed
(74) *Attorney, Agent, or Firm* — Collard & Roe, P.C.

(57) ABSTRACT

A device for treating a surface, in particular to a cleaning robot, has a detection device for identifying the type of surface, which detection device has a light source for irradiating the surface with light and has a sensor for detecting the light which is reflected by the surface. In order to improve the identification of the type of surface, it is proposed that a three-dimensional screen panel which forms a plurality of partial volumes is associated with the sensor, wherein each partial volume is in each case associated with a different sensor subarea of the sensor, and wherein adjacent sensor subareas are optically separated from one another by means of the screen panel such that light is prevented from passing from a first partial volume to a second partial volume. Furthermore, the invention relates to a method for operating a device for treating a surface.

10 Claims, 4 Drawing Sheets

(51) Int. Cl.
  *G01N 21/47*  (2006.01)
  *G01N 21/57*  (2006.01)
(52) U.S. Cl.
  CPC ............ *G01N 21/57* (2013.01); *A47L 9/2831* (2013.01); *A47L 2201/04* (2013.01); *A47L 2201/06* (2013.01); *G01N 2201/0642* (2013.01)
(58) Field of Classification Search
  CPC . A47L 2201/04; A47L 2201/06; G01N 21/47; G01N 21/57; G01N 21/4738; G01N 2201/0642
  See application file for complete search history.

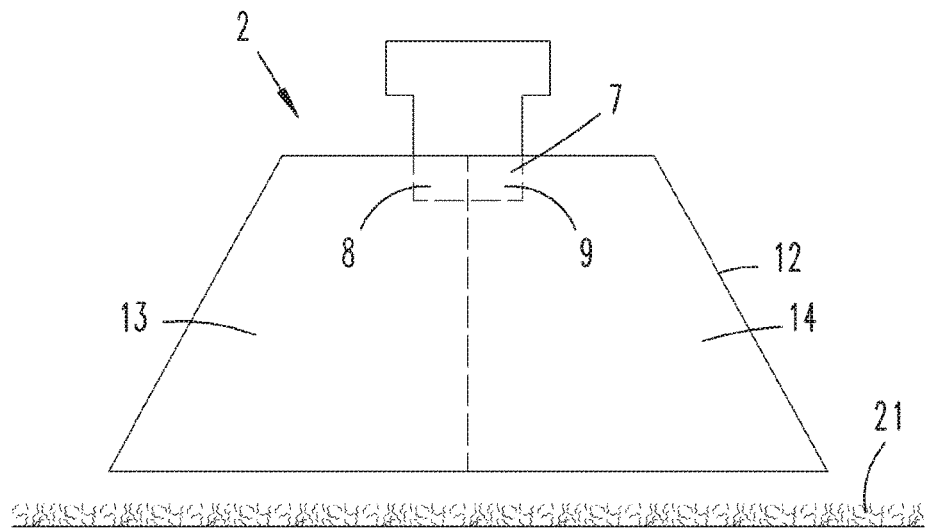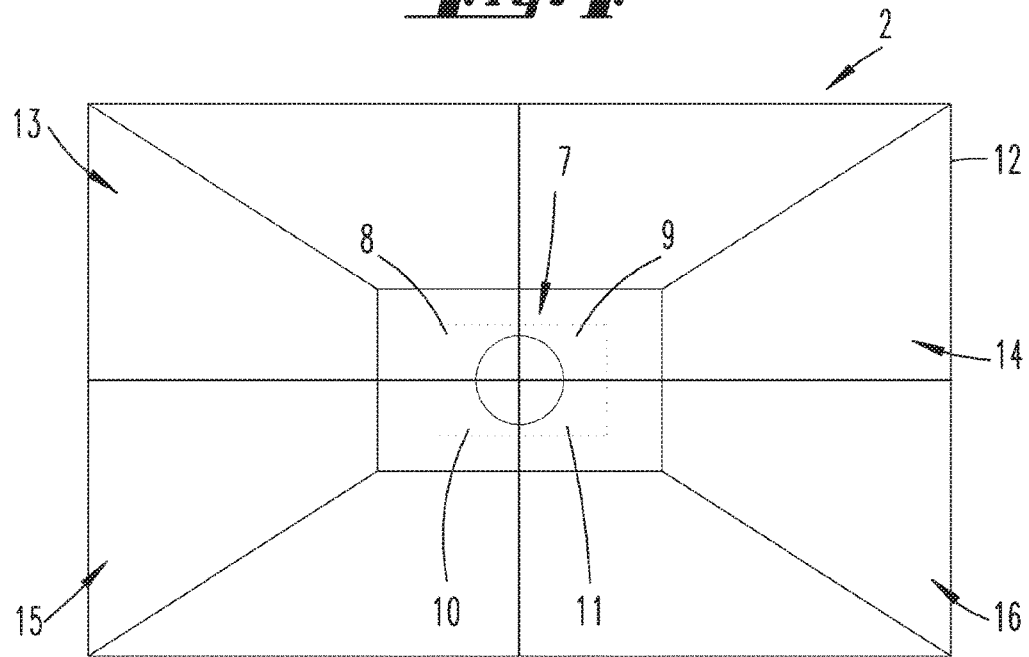

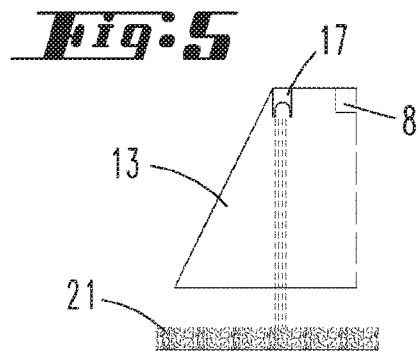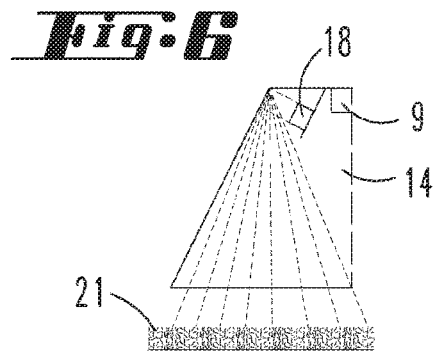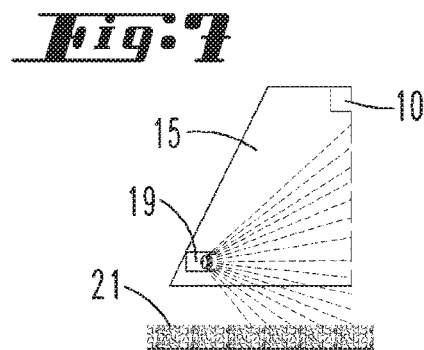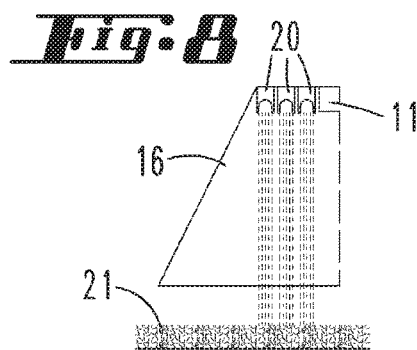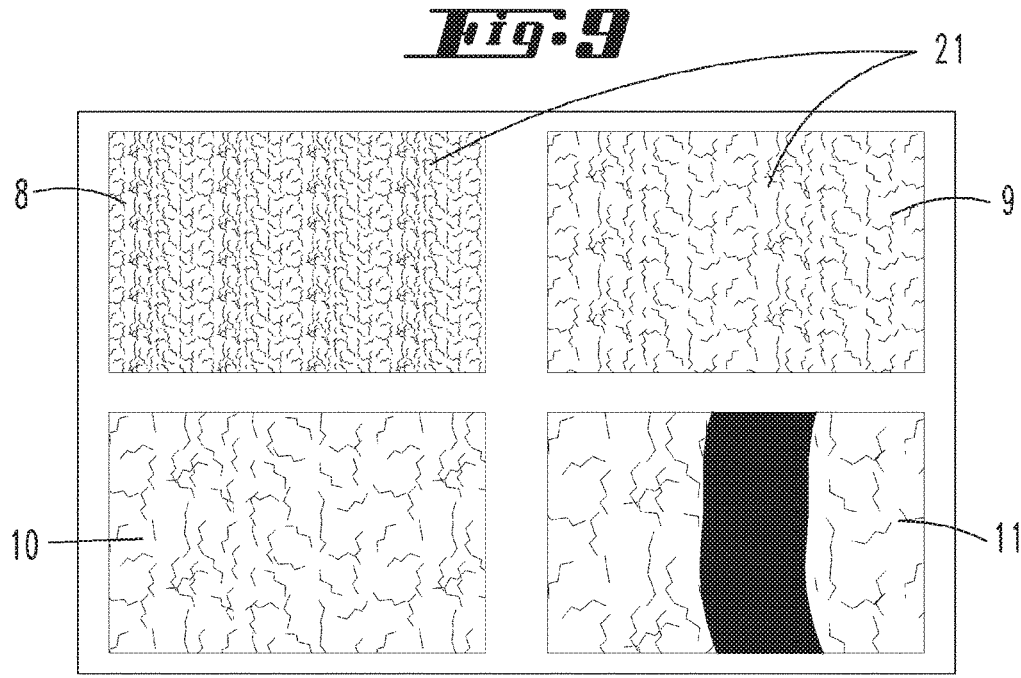

Fig. 10

| Segment | Description of the feature | Carpet | Wood | PVC |
|---|---|---|---|---|
| S1 | Gloss point | NO | YES | YES |
| S2 | Wood-typical hue | NO | YES | NO |
| | Preferential direction of the texture | NO | YES (grain) | NO |
| S3 | Portion of black pixels of the image | High | Low | Low |
| S4 | Smoothness of the light-dark transitions | Low | High | Average |

# DEVICE FOR TREATING A SURFACE

CROSS REFERENCE TO RELATED APPLICATIONS

This application is the National Stage of PCT/EP2016/065693 filed on Jul. 4, 2016, which claims priority under 35 U.S.C. § 119 of German Application No. 10 2015 112 174.3 filed on Jul. 27, 2015, the disclosures of which are incorporated by reference. The international application under PCT article 21(2) was not published in English.

FIELD OF TECHNOLOGY

The invention relates to a device for treating a surface, in particular to a cleaning robot, having a detection device for identifying the type of surface, which detection device has a light source for irradiating the surface with light and a sensor for detecting the light, which is reflected by the surface.

PRIOR ART

Devices of the above-mentioned type are well known in the prior art, thus in particular in the form of automatically movable cleaning robots for cleaning and/maintaining floors or floor coverings. For example, it can be a vacuum cleaner and/or a wet mop.

Publication DE 10 2013 113 426 A1 (also published as US 2014/0166047 A1) relates for example to a cleaning device comprising a device for creating photographs of a surface to be navigated, wherein a photo can be evaluated with regard to the type of a floor covering, and wherein an identified floor covering can be used with regard to a movement strategy of the cleaning device and/or with regard to a setting of cleaning parameters, such as distance to the floor, brush speed or the like.

Even though this cleaning device has proven itself in the prior art, a continuous further development is nonetheless desired.

SUMMARY OF THE INVENTION

Based on the above-mentioned prior art, it is the object of the invention to create a device comprising a detection device for identifying the type of surface, in the case of which the type of surface can be identified with an even greater accuracy.

To solve the above-mentioned object, the invention proposes that a three-dimensional screen panel, which forms a plurality of partial volumes, is associated with the sensor of the detection device, wherein each partial volume is in each case associated with a different sensor subarea of the sensor, and wherein adjacent sensor subareas are optically separated from one another by means of the screen panel such that light is prevented from passing from a first partial volume to a second partial volume.

The screen panel thus serves as optical screen, which divides the sensor into a plurality of, for example four, sensor subareas and which optically, i.e. photometrically, separates the individual sensor subareas at the same time, so that the light reflected from the surface hits only a sensor subarea of the sensor within only a partial volume of the screen panel. It is thus possible to embody the detection device with a measuring accuracy, which is increased as compared to the prior art, by means of only a single sensor, because the latter is divided by means of the screen panel into individual sensor subareas, which provide for a separate evaluation of the light, which hits the respective sensor subarea. The detection device can thus be produced in a particularly simple and cost-efficient manner. In addition, it is not required to read out the measuring data of a plurality of sensors—simultaneously or consecutively—which impacts the duration of a measuring cycle. During a measurement, the screen panel is preferably arranged near the floor above the surface to be treated, so that the entry of ambient light into the partial volumes of the screen panel is minimized and only the light reflected on the surface by the light source of the detection device contributes to the measurement, which ultimately improves the reliability of the identification of the type of surface.

It is furthermore proposed that a separate light source is associated with each partial volume of the screen panel. By assigning a separate light source for each partial volume of the screen panel, in particular for each partial volume, the surface to be treated is illuminated separately with regard to each partial volume of the screen panel. The screen panel can furthermore be attached directly to the surface, so that ambient light can no longer enter into the screen panel from the outside. By associating a separate light source with each partial volume, the corresponding subareas of the surface can be illuminated in the same or in a different manner, so that an identical illuminating situation is or is not created within the different partial volumes.

In the alternative, it is proposed that a common light source is associated with the screen panel, wherein a separate light exit element of the light source, in particular an optical fiber, is associated with each partial volume. According to this embodiment, it is not necessary for a separate light source to be installed for each partial volume. In fact, a common light source, the emitted light of which is guided into the individual partial volumes by means of light-guiding elements, can be associated with all partial volumes. Advantageously, the light source is thereby arranged outside of the partial volumes, so that this thus does not result in a loss of space. For example, the light source can be arranged outside of the screen panel, advantageously also on the device housing of the treatment device, wherein the light is coupled into each individual partial volume by means of a light-guiding element (optical fiber). Advantageously, the light-guiding elements are optical fibers, because they are particularly cost-efficient and can be flexibly adapted to the spatial situations of the screen panel or also of the device housing, respectively. Compared to the arrangement of a separate light source for each partial volume of the screen panel, a cost-efficient production of the detection device and thus also of the device for treating the surface, can be attained by means of the common light source.

It is proposed that the light within the partial volume has a certain illuminating parameter for irradiating the surface, wherein the illuminating parameters within at least two partial volumes differ from one another. As a result of this embodiment, the subareas of the illuminated surface can be illuminated in different ways, so that different features of the surface can be detected and the measuring results of the different partial volumes or sensor subareas, respectively, can be combined to form a measuring result, which is more reliable as a whole. The surface to be measured is thus not only illuminated with light of a single illuminating parameter, but with a plurality of different illuminating parameters, for example with four different illuminating parameters in the case of four sensor subareas. As a result of this embodiment, a plurality of different surface types can be differentiated with an ever higher accuracy. As a result of the different illuminating parameters it is in particular also possible to not only differentiate hard floors from carpeted floor, but in fact for example also differentiate hard floors among one another, so that a quantity of moisture, which differs for each hard floor type, for example, is applied to the surface, without damaging the surface by a moisture, which is too high. As a result of the use of different illuminating parameters within the illuminating panel, features of the surface, which do not become visible for example within a second partial volume with a second illuminating parameter, emerge within a partial volume with a first illuminating parameter. Depending on the type of surface, a certain type of illumination can thus make the emergence of a feature of the surface more difficult or easier. As a result of the illumination of the surface with a plurality of different illuminating parameters, a plurality of simultaneous measuring results is thus created, which, in the special combination, allow drawing an even more reliable conclusion to the type of surface. As a result of the illuminating panel, the measurement with different illuminating parameters is thus made possible, without the light portions of the individual partial volumes influencing one another. Every light portion is thereby associated with a certain sensor subarea of a single, common sensor, which significantly reduces the apparatus configuration of the detection device. In the event of identical illuminating parameters, the adjacent subareas of the surface to be treated can for example be illuminated at the same angle to the light source and the sensor, so that the measuring results of the partial volumes can be compared to one another and so that deviations of the subareas can possibly be determined in order to avoid the measuring of an artifact, which is not typical for the surface to be treated.

It is proposed that the illuminating parameter is an angle-dependent radiant intensity of the light, an entry angle of the light onto the irradiated surface, an angle between the light source and the sensor and/or between the light exit area and the sensor, a distance of the light source and/or of the light exit area to the irradiated surface, a polarization state of the light and/or an isotropy of the light. As a result of these illuminating parameters, the surface is irradiated by means of the light source or by means of the light exit area of the light source, respectively within each partial volume at a certain entry angle, a certain wavelength, polarization, isotropy or the like. Isotropy of the light is to be understood as a different direction of the beams of a beam bundle, wherein a parallelism of the beams of a beam bundle is at hand in the case of a low isotropy. In the case of completely isotropic light, the beams of a beam bundle, in contrast, are not parallel to one another. The isotropy of the light can for example be attained by means of a reflection of the light emitted by the light source/the light exit area at a rough surface. To provide different illuminating parameters, a punctiform light source can also be used for example within a first partial volume, while a flat light source is used in a second partial volume. The surface can furthermore be illuminated directly or indirectly. The surface can be illuminated perpendicularly or at an angle unequal to 90°. It is furthermore also possible to illuminate the surface with a stripe pattern. This can be attained, for example, in that a slit diaphragm is associated with the light source. Further illuminating parameters are conceivable.

It is furthermore proposed that an evaluation device, which is equipped to evaluate the light received by means of the sensor subarea, with regard to a certain surface parameter, in particular a gloss, a color and/or a texture of the surface, is associated with the sensor. Advantageously, the evaluation device has a microprocessor and a storage for storing measuring data as well as reference data of known surfaces. The evaluation device can either be arranged in the detection device itself or at a different subarea of the device for treating the surface. The evaluation device evaluates the received light with regard to certain surface parameters, so that different features of the surface to be identified are evaluated. These features can emerge for example only in the case of hard floors and/or can only be relevant for carpeted floors. To determine the surface parameters, a certain illuminating parameter may possibly be necessary within the associated partial volume. To determine the color of the surface, for example, an illumination with white light is advisable. To identify a microscopic structure of the surface, the use of light of a certain wavelength can furthermore also be necessary.

The surface parameter can for example be a gloss, a color and/or a texture of the surface. For example, the measuring signal received by the sensor subarea can thus be evaluated within a first partial volume of the screen panel with regard to a gloss point, a wavelength-dependent reflection maximum, reflection spectrum or the like, so that a conclusion can be drawn to the type of surface. The existence of a gloss point, for example, refers to a hard floor, because carpeted floors typically do not show a gloss point. In the alternative or in addition, the color can also allow drawing a conclusion to a certain surface type. The texture of the surface is furthermore also of interest, because for example carpets or carpeted floors, respectively, show a different surface structure than for example hard floors.

It is proposed that the evaluated surface parameters of at least two sensor subareas are different from one another. A different surface parameter is thus determined in each of the partial volumes of the screen panel, so that the totality of the evaluated surface parameters within the entire screen panel leads to an overall reliable identification of the type of surface. The more partial volumes or sensor subareas, respectively, the detection device has thereby, the more accurately the type of surface can be identified.

It is proposed that the evaluation device is equipped to logically link the surface parameters of at least two sensor subareas to one another and to compare them to reference data of known surfaces in order to determine the type of surface. By combining the surface parameters of a plurality of sensor subareas, a logical combination is created, which is characteristic for the certain type of a surface. By using the evaluation device, the measured combination is compared with reference data, which include combinations of surface parameters stored in the data storage. The currently measured surface can thus be identified reliably. The larger the number of the measured surface parameters, the more reliable the type of surface can be identified.

It is furthermore proposed that the sensor is a camera chip, in particular a CCD sensor or a CMOS sensor. The sensor surface of the camera chip is thereby evaluated as a function of the arrangement of the individual partial volumes, wherein, for example in the case of four partial volumes, the sensor surface is also divided into four sensor subareas, advantageously of the same size. Each sensor subarea is thereby evaluated and/or read out coherently by the evaluation device, so that the measured surface parameter can be assigned unambiguously to a certain partial volume of the screen panel.

In addition to the above-described device for treating a surface, a method for operating a device, in particular an above-described device, is also proposed with the invention, in the case of which the surface is irradiated with light, and light reflected from the surface is evaluated to identify the type of surface. The method according to the invention includes that light is determined in a plurality of optically separated partial volumes of a three-dimensional screen panel associated with a sensor, is irradiated onto the surface, and is reflected from the surface onto a sensor subarea of the sensor, which is associated with the respective partial volume, wherein an illuminating parameter of the light emitted within a first partial volume differs from an illuminating parameter of the light emitted within a second partial volume, and wherein the light received by the sensor subareas is evaluated with regard to surface parameters of the surface, which differ from one another. The execution and the features of the method thereby follow analogously to the explanations provided above with regard to the device for treating the surface.

BRIEF DESCRIPTION OF THE DRAWINGS

The invention will be described in more detail below by means of exemplary embodiments.

FIG. 3 shows a side view of a detection device,
FIG. 4 shows a bottom view of the detection device,
FIG. 5 shows a first partial volume of the screen panel,
FIG. 6 shows a second partial volume of the screen panel,
FIG. 7 shows a third partial volume of the screen panel,
FIG. 8 shows a fourth partial volume of the screen panel,
FIG. 9 shows an image captured by the sensor,
FIG. 10 shows a table with reference data for evaluation.

DESCRIPTION OF THE PREFERRED EMBODIMENTS

Figure 1:
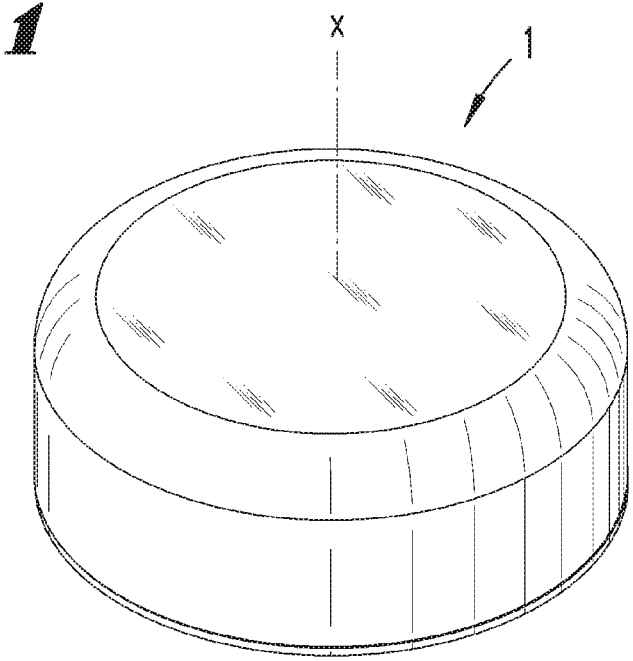
FIG. 1 shows a device according to the invention in a perspective view.

FIG. 1 shows a device 1 according to the invention, which is embodied here as automatically movable robotic vacuum cleaner. The device 1 has travel wheels as well as an electric motor for driving the travel wheels. The device 1 can furthermore be equipped with a navigation device (not illustrated), which provides for the automatic orientation of the device 1 within a room. Said navigation device typically includes a device for identifying obstacles and room situations.

Figure 2:
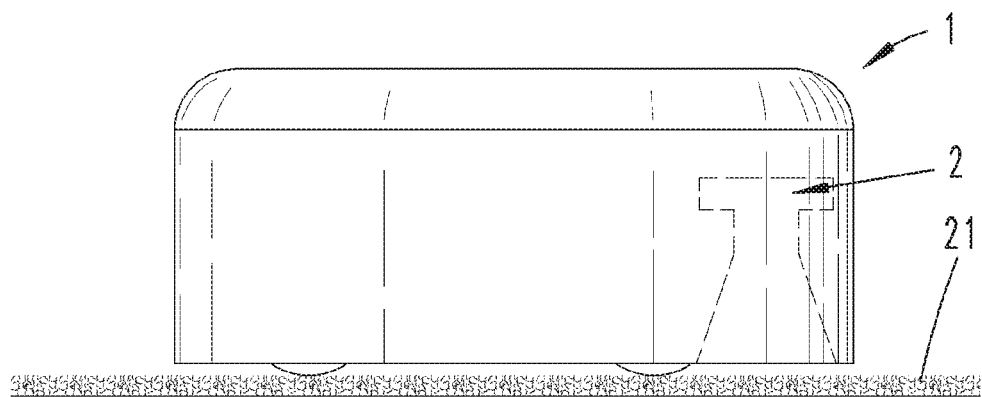
FIG. 2 shows the device in a side view.

FIG. 2 shows the device 1 in a side view, wherein a detection device 2, which is installed in the device 1, for identifying the type of surface 21 is illustrated in a dashed manner. With a detection side, the detection device 2 is directed towards the surface 21 to be measured, here for example a carpeted floor.

FIG. 3 shows the detection device 2 in a schematic side view. The detection device 2 has a sensor 7, here a camera, comprising a camera chip (CCD chip), as well as a three-dimensional screen panel 12, which is embodied in a screen-like manner and which supports the sensor 7 on its upper side. The screen panel 12 has a plurality of partial volumes 13, 14, 15, 16, of which only two partial volumes 13, 14 can be identified in the illustrated side view. A certain sensor subarea 8, 9, 10, 11 of the sensor 7 is associated with each of the partial volumes 13, 14, 15, 16. A separate light source 17, 18, 19, 20 is furthermore arranged in each partial volume 13, 14, 15, 16 (see FIGS. 5 to 8). The screen panel 12 is embodied in such a way that the partial volumes 13, 14, 15, 16 are optically separated from one another by walls of the screen panel 12 in such a way that no light can propagate between the partial volumes 13, 14, 15, 16, i.e. light emitted in a certain partial volumes 13, 14, 15, 16 cannot pass into another partial volume 13, 14, 15, 16. The partial volumes 3, 14, 15, 16 are to be thus understood as areas of the screen panel 12, which are photometrically separated and in which a separate light source 17, 18, 19, 20 in each case emits light here, irradiates onto a subarea of the surface 21 to be identified, and wherein a sensor subarea 8, 9, 10, 11, which is irradiated with the light reflected from the surface 21 of the sensor 7, is associated with each partial volume 13, 14, 15, 16.

FIG. 4 shows the detection device 2 from below, i.e. viewed from the direction of the surface 21 into the screen panel 12. The individual partial volumes 13, 14, 15, 16 of the screen panel 12 can be seen, which are in each case associated with a sensor subarea 8, 9, 10, 11 of the sensor 7.

FIGS. 5 to 8 in each case show one of the partial volumes 13, 14, 15, 16 in a vertical section. The light emitted by the respective light source 17, 18, 19, 20 has an illuminating parameter, which is characteristic for the respective partial volume 13, 14, 15, 16, for irradiating the surface 21. Different illuminating conditions of the surface 21 can thus be created within the partial volumes 13, 14, 15, 16, and can be detected by means of only one sensor 7 (which is common to all partial volumes 13, 14, 15, 16). Due to the different illuminating parameters, different surface parameters, which are characteristic for the currently measured surface 21, emerge on the respective sensor subarea 8, 9, 10, 11. The signals received as a whole by the sensor 7 can be joined logically with one another and can be connected to form a total data set, which provides insight into the type of surface 21.

FIG. 5 shows a first partial volume 13 of the screen panel 12, in which a first light source 17 and a first sensor subarea 8 are arranged. The light source 17 is arranged within the partial volume 13 in such a way that said light source perpendicularly irradiates the surface 21 to be identified. The light source 17 thereby irradiates only a limited subarea of the surface 21, which only has a small surface portion relative to the exit surface of the partial volume 13 of the screen panel 12. Depending on the type of surface 21, a certain portion of the light can reach from the surface 21 to the sensor subarea 8. If the surface 21 is a carpeted floor, for example, the light is scattered on the surface 21, so that a diffuse light portion hits the sensor subarea 8. If, in contrast, it is a hard floor, the perpendicularly irradiated surface 21 reflects the light back substantially perpendicularly, so that only a relatively small light portion hits the sensor subarea 8. Based on the so-called "gloss point", hard floors can thus be differentiated from carpeted floors.

FIG. 6 shows a second partial volume 14, in which a second light source 18 as well as a second sensor subarea 9 are arranged. The light source 18 is arranged within the partial volume 14 in such a way that the surface 21 is not irradiated directly. In fact, the light source 18 is directed to a corner area of the partial volume 14, so that the radiation emitted by the light source 18 is reflected from the inner wall of the screen panel 12 and illuminates the surface 21 in a scattered and indirect manner. In addition, the light emitted by the light source 18 is widened at the corner area, so that the irradiation, which hits the surface 12, hits the surface 21 from different angles within a widened cone of light. The scattered irradiation of different surfaces 21, such as, for example, hard floors and carpeted floors, or also different hard floors and/or carpeted floors among one another, in turn, causes different reflection signals, so that a conclusion can be drawn to the type of surface 21 by means of the light received by the sensor subarea 9. Here, the arrangement within the partial volume 14 serves to identify a wood-typical hue, i.e. to identify the surface parameter "color", and to identify the texture of the surface 21. If the texture has a preferential direction, for example, a conclusion can very likely be drawn that the surface 21 is a carpeted floor or a vinyl flooring. In fact, a wooden floor is possible as surface 21, which has a grain.

FIG. 7 shows a third partial volume 15 comprising a third light source 19 and a third sensor subarea 10. The light source 19 is oriented substantially parallel to the surface 21 with the optical axis, wherein the emitted light partially hits the surface 21 directly at an oblique angle due to the conically widened light bundle, and a different portion is reflected on a wall of the screen panel 12, and possible hits the surface 21 in a scattered manner. The sensor subarea 10 receives the light reflected from the surface 21, which will be analyzed here, for example with regard to the surface parameter "portion of black pixels". If the light signal received by the sensor subarea 10 has a particularly large portion of black pixels, a conclusion can be drawn to a carpeted floor. If the portion of black pixels is small, a wood or PVC is possible as surface 21, in contrast.

FIG. 8 shows the fourth partial volume 16 of the screen panel 12, in which three light sources 20 as well as one sensor subarea 11 are arranged. The light sources 20 are arranged in parallel to one another, so that the emitted light portions run substantially parallel to one another, and the light hits the surface 21 in a strip-shaped manner. This creates a strip pattern on the surface 21, which is to be identified, the light/dark transitions of which allow drawing a conclusion to the type of surface 21. If the surface 21 is a carpeted floor, for example, the transitions have an irregular structure. The smoother the surface 21, however, the sharper the light/dark transitions, for example in the case of PVC or in particular wood.

FIG. 9 shows the light signals detected as a whole by the sensor 7 in the form of a camera image. The latter is separated with regard to the individual sensor subareas 8, 9, 10, 11. Due to the different illuminating parameters within the partial volumes 13, 14, 15, 16, each sensor subarea signal thereby reflects a different surface parameter. The corresponding signals of the sensor subareas 8, 9, 10, 11 are illustrated here. The image associated with the sensor subarea 8 serves to determine the gloss point, the image associated with the sensor subarea 9 serves to determine the texture, the image associated with the sensor subarea 10 serves to determine the portion of the black pixels in the image, and the image associated with the sensor subarea 11 serves to evaluate the light/dark transitions. It can be seen here, for example, that the surface 21 does not show a gloss point, does not have a preferential direction of the texture, has a large portion of black pixels, and the light/dark transitions are not straight lines. These surface parameters are logically connected to one another to form a total data set and, in order to determine the type of surface 21, are compared to reference data of known surfaces 21, which are stored within a data storage of an evaluation device. If the currently measured data set corresponds to a stored data set, the type of surface 21 can be determined reliably. The reference data stored in the data storage can be stored as table. In the above-specified case, a table appears in the way, which is illustrated in FIG. 10, for example.

Advantageously, the method for identifying the type of surface 21 is carried out while the device 1 travels across the surface 21. The sensor 7 thereby operates continuously. With regard to each partial volume 13, 14, 15, 16, a certain surface parameter is extracted. The surface parameters are logically connected to one another and are used to identify the surface 21.

On principle, methods of supervised learning are used for the evaluation. These methods include for example a training phase, in which a plurality of different surfaces 21 is shown to the evaluation device. The respective surfaces 21 are known and are stored inside the data storage with their corresponding surface parameters. It is also possible thereby that not only known surface parameters can be identified, but also different similar surface parameters, which the evaluation device can associate automatically. Different types of a surface 21, the surface parameters of which are not identical, but similar, can thus also be identified, so that the evaluation device can associate them to a certain type of surface 21.

The further treatment of the surface 21 by means of the device 1 can then be controlled with the knowledge of the type of the currently measured surface 21. If the identified surface 21 is a carpeted floor, the device 1 will avoid moistening the surface 21, for example, and will limit a cleaning process to a vacuuming and/or brushing, for example.

REFERENCE LIST 1 device
2 detection device
3 light source
4 light source
5 light source
6 light source
7 sensor
8 sensor subarea
9 sensor subarea
10 sensor subarea
11 sensor subarea
12 screen panel
13 partial volume
14 partial volume
15 partial volume
16 partial volume
17 light source
18 light source
19 light source
20 light source
21 surface

The invention claimed is:

1. A device (1) for treating a surface (21), having a detection device (2) for identifying the type of surface (21), which detection device (2) has a light source (3, 4, 5, 6) for irradiating the surface (21) with light and a sensor (7) for detecting the light, which is reflected by the surface (21), wherein a three-dimensional screen panel (12), which forms a plurality of partial volumes (13, 14, 15, 16), is associated with the sensor (7), wherein each partial volume (13, 14, 15, 16) is in each case associated with a different sensor subarea (8, 9, 10, 11) of the sensor (7), and wherein adjacent sensor subareas (8, 9, 10, 11) are optically separated from one another by means of the screen panel (12) such that light is prevented from passing from a first partial volume (13, 14, 15, 16) to a second partial volume (13, 14, 15, 16).

2. The device (1) according to claim 1, wherein a separate light source (17, 18, 19, 20) is associated with each partial volume (13, 14, 15, 16) of the screen panel (12).

3. The device (1) according to claim 1, wherein a common light source (17, 18, 19, 20) is associated with the screen panel, wherein a separate light exit element of the light source (17, 18, 19, 20), in particular an optical fiber, is associated with each partial volume (13, 14, 15, 16).

4. The device (1) according to claim 1, wherein the light within the partial volume (13, 14, 15, 16) has a certain illuminating parameter for irradiating the surface (21), wherein the illuminating parameters within at least two partial volumes (13, 14, 15, 16) differ from one another.

5. The device (1) according to claim 4, wherein the illuminating parameter is an angle-dependent radiant intensity of the light, an entry angle of the light onto the irradiated surface (21), an angle between the light source (3, 4, 5, 6) and the sensor (7) and/or between the light exit area and the sensor (7), a distance of the light source (3, 4, 5, 6) and/or of the light exit area to the irradiated surface (21), a polarization state of the light and/or an isotropy of the light.

6. The device (1) according to claim 1, wherein an evaluation device, which is equipped to evaluate the light received by means of the sensor subarea (8, 9, 10, 11), with regard to a certain surface parameter, is associated with the sensor (7).

7. The device (1) according to claim 6, wherein the evaluated surface parameters of at least two sensor subareas (8, 9, 10, 11) are different from one another.

8. The device (1) according to claim 6, wherein the evaluation device is equipped to logically link the surface parameters of at least two sensor subareas (8, 9, 10, 11) to one another and to compare them to reference data of known surfaces (21) in order to determine the type of surface (21).

9. The device (1) according to claim 1, wherein the sensor (7) is a camera chip.

10. A method for operating a device (1) for treating a surface (21), wherein the surface (21) is irradiated with light, and light reflected from the surface (21) is evaluated to identify the type of surface (21), wherein light is determined in a plurality of optically separated partial volumes (13, 14, 15, 16) of a three-dimensional screen panel (12) associated with a sensor (7), is irradiated onto the surface (21), and is reflected from the surface (21) onto a sensor subarea (8, 9, 10, 11) of the sensor (7), which is associated with the respective partial volume (13, 14, 15, 16), wherein an illuminating parameter of the light emitted within a first partial volume (13, 14, 15, 16) differs from an illuminating parameter of the light emitted within a second partial volume (13, 14, 15, 16), and wherein the light received by the sensor subareas (8, 9, 10, 11) is evaluated with regard to surface parameters of the surface (21), which differ from one another.

* * * * *